(12) United States Patent
Yamane (10) Patent No.: US 10,370,384 B2
(45) Date of Patent: Aug. 6, 2019

(54) METHOD FOR PRODUCING DIOL HAVING CYCLIC ACETAL SKELETON

(71) Applicant: Mitsubishi Gas Chemical Company, Inc., Chiyoda-ku (JP)

(72) Inventor: Masahiro Yamane, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/078,292

(22) PCT Filed: Mar. 9, 2017

(86) PCT No.: PCT/JP2017/009403
§ 371 (c)(1),
(2) Date: Aug. 21, 2018

(87) PCT Pub. No.: WO2017/159525
PCT Pub. Date: Sep. 21, 2017

(65) Prior Publication Data
US 2019/0055259 A1    Feb. 21, 2019

(30) Foreign Application Priority Data
Mar. 15, 2016    (JP) .................. 2016-050882

(51) Int. Cl.
*C07D 319/00*    (2006.01)
*C07D 493/10*    (2006.01)
*C07D 319/06*    (2006.01)
*C07C 45/45*    (2006.01)
*C07C 45/79*    (2006.01)
*C07C 45/80*    (2006.01)
(Continued)

(52) U.S. Cl.
CPC ............ *C07D 493/10* (2013.01); *C07C 45/45* (2013.01); *C07C 45/79* (2013.01); *C07C 45/80* (2013.01); *C07C 45/81* (2013.01); *C07C 45/82* (2013.01); *C07D 319/06* (2013.01)

(58) Field of Classification Search
CPC .... C07D 493/10; C07D 319/06; C07D 45/82; C07D 45/79; C07D 45/81; C07D 45/80; C07D 45/45
USPC ....................................... 549/335
See application file for complete search history.

(56) References Cited

U.S. PATENT DOCUMENTS

| 9,061,985 B2 | 6/2015 | Matsuura et al. |
| 2007/0032682 A1 | 2/2007 | Amemiya et al. |
| 2007/0078271 A1 | 4/2007 | Watanabe et al. |

FOREIGN PATENT DOCUMENTS

| JP | 59-134788 A | 8/1984 |
| JP | 59-148776 A | 8/1984 |
| JP | 3-27384 A | 2/1991 |

(Continued)

*Primary Examiner* — Taylor V Oh
(74) *Attorney, Agent, or Firm* — Oblon, McClelland, Maier & Neustadt, L.L.P.

(57) ABSTRACT

The present invention provides a method for producing a diol having a cyclic acetal skeleton, in which the method include an acetalization reaction step of obtaining a diol having a cyclic acetal skeleton by subjecting raw material hydroxypivalaldehyde and at least pentaerythritol and/or trimethylolpropane to an acetalization reaction under an acid catalyst and the raw material hydroxypivalaldehyde can contain a prescribed amount of at least one impurity selected from the group consisting of formaldehyde, neopentyl glycol, an ester compound having a neopentyl glycol skeleton represented by formula (III), and isobutyraldehyde.

9 Claims, 1 Drawing Sheet

(51) Int. Cl.
*C07C 45/81* (2006.01)
*C07C 45/82* (2006.01)

(56) References Cited

FOREIGN PATENT DOCUMENTS

| | | |
|---|---|---|
| JP | 2000-34290 A | 2/2000 |
| JP | 2001-55388 A | 2/2001 |
| JP | 2001-302673 A | 10/2001 |
| JP | 2001-302674 A | 10/2001 |
| JP | 2005-29563 A | 2/2005 |
| JP | 2007-70339 A | 3/2007 |
| JP | 2007-126448 A | 5/2007 |
| JP | 2011-74000 A | 4/2011 |
| WO | WO 2012/118196 A1 | 9/2012 |

METHOD FOR PRODUCING DIOL HAVING CYCLIC ACETAL SKELETON

TECHNICAL FIELD

The present invention relates to a method for producing a diol having a cyclic acetal skeleton.

BACKGROUND ART 3,9-Bis(1,1-dimethyl-2-hydroxyethyl)-2,4,8,10-tetraoxaspiro[5.5]undecane (hereinafter also referred to as "spiroglycol") is used mainly as a resin raw material. A spiroglycol is conventionally synthesized by subjecting hydroxypivalaldehyde (hereinafter also referred to as "HPA") and pentaerythritol (hereinafter also referred to as "PE") to an acetalization reaction under an acid catalyst in an aqueous solution. Then, after neutralizing the resultant reaction solution with an alkali, crystals of the spiroglycol precipitated during the reaction are filtered, washed with water and dried to obtain a product.

As a production method for such a spiroglycol, for example, a method in which HPA is reacted with PE in a water solvent using an acid catalyst to obtain a reaction product solution, the reaction product solution is neutralized with an alkali, and the neutralized reaction product solution is heated to 75 to 100° C. to produce a spiroglycol (see, for example, Patent Literature 1); a method in which HPA is reacted with PE in a water solvent using an acid catalyst to obtain a reaction product solution, the reaction product solution is adjusted to pH 7 or more with an alkali to obtain a slurry mixture, and the thus obtained slurry mixture is subjected to a heat treatment at 120° C. or more to produce a spiroglycol (see, for example, Patent Literature 2); and a method in which HPA is reacted with PE using an acid catalyst in a mixed solvent containing an organic solvent immiscible with water and water to produce a spiroglycol (see, for example, Patent Literature 3), which have been proposed. It is noted that HPA used as a raw material is conventionally obtained through an aldol condensation reaction of isobutyraldehyde and formaldehyde performed in the presence of a basic catalyst.

Besides, as a method for industrially advantageously producing a spiroglycol having a sufficiently high purity, a production method for a spiroglycol has been known, where PE is reacted with HPA using an acid catalyst to obtain a reaction solution (slurry) containing a prescribed amount of a spiroglycol, the reaction solution is filtered without neutralization to separate the spiroglycol, and a part of the thus obtained filtrate is reused in the reaction of the next cycle has been known (see, for example, Patent Literature 4). Furthermore, as a method for producing a spiroglycol having a sufficient purity, a method has been known, where a crude spiroglycol obtained through a reaction of PE and HPA is dissolved in an organic solvent, water is added to the thus obtained solution for extracting and removing an impurity into water, an aqueous layer and an organic layer are separated, and the organic layer is cooled to recrystallize a spiroglycol (see, for example, Patent Literature 5). In addition, as a method for producing a spiroglycol having a sufficiently high purity, a production method for a spiroglycol including a step of bringing hydroxypivalaldehyde used as a raw material of a spiroglycol into contact with an oxygen-containing gas in advance has been known (see, for example, Patent Literature 6).

CITATION LIST

Patent Literature

Patent Literature 1: Japanese Patent Laid-Open No. S59-148776
Patent Literature 2: Japanese Patent Laid-Open No. H03-27384
Patent Literature 3: Japanese Patent Laid-Open No. 2001-55388
Patent Literature 4: Japanese Patent Laid-Open No. 2005-29563
Patent Literature 5: Japanese Patent Laid-Open No. 2000-34290
Patent Literature 6: Japanese Patent Laid-Open No. 2001-302673

SUMMARY OF INVENTION

Technical Problem

When a spiroglycol having a low purity is used as a polymer raw material or the like, the properties peculiar to the spiroglycol cannot be attained. For example, copolymerized polycarbonate obtained from a bisphenol and a spiroglycol originally has excellent optical properties and impact resistance, and hence is useful as a resin for optical use, but a polymer obtained by polymerization using a conventionally commercially available spiroglycol having a low purity cannot attain a satisfactory impact resistance property and also has a problem in coloring, and hence cannot be used for optical use. For these reasons, the purity of a spiroglycol is preferably as high as possible.

When the method described in Patent Literature 4 is employed, however, if at least a part of the filtered reaction solution is reused in the reaction of the next cycle, side reaction products derived from impurities such as formaldehyde contained in HPA used as a raw material are accumulated as the number of cycles of performing the reaction increases. When the amount of these side reaction products exceeds a prescribed value, the side reaction products are precipitated in the spiroglycol, causing a problem that the purity of the spiroglycol to be obtained is lowered.

Besides, the method of Patent Literature 5 has a problem that a large purification cost is industrially required.

Furthermore, in Patent Literature 6, the relationship between the amount of impurities contained in the raw material HPA and the amount of impurities contained in the spiroglycol obtained by the spiroglycol synthesis is not sufficiently examined.

This problem can similarly apply to a diol having a cyclic acetal skeleton such as 5-methylol-5-ethyl-2-(1,1-dimethyl-2-hydroxyethyl)-1,3-dioxane (hereinafter also referred to as "dioxane glycol").

The present invention was devised in consideration of these problems, and an object is to provide a method for producing a diol having a cyclic acetal skeleton capable of producing a high purity diol having a cyclic acetal skeleton by recognizing the relationship between impurities contained in HPA used as a raw material of the diol having a cyclic acetal skeleton and impurities contained in the diol having a cyclic acetal skeleton obtained by a synthesis reaction for controlling the amount of the impurities contained in the raw material HPA.

Besides, in the methods described in Patent Literatures 1 to 3 and 5, a filtrate generated by filtering the crystals of the spiroglycol (hereinafter also referred to as the "reaction mother liquor") is discarded after neutralizing the acid catalyst. In other words, useful components contained in the reaction mother liquor, that is, HPA, PE and a reaction intermediate of 5,5-dihydroxymethyl-2-(1,1-dimethyl-2-hydroxyethyl)-1,3-dioxane (hereinafter also referred to as "DOT"), are discarded. Furthermore, this reaction mother liquor is several times in amount as large as the spiroglycol to be generated, and hence the treatment thereof requires much labor. Therefore, the discard of the reaction mother liquor is industrially disadvantageous.

Similarly, also when purification is performed by crystallization using an organic solvent, since a filtrate generated by filtering (hereinafter also referred to as the "crystallization mother liquor") contains a large amount of spiroglycol, discard thereof means discard of the spiroglycol and hence is industrially disadvantageous.

In order to overcome such a situation, the reaction mother liquor may be reused without neutralization in the reaction of the next cycle in the step of synthesizing the spiroglycol, but when the reaction mother liquor is reused in the reaction of the next cycle, reaction intermediates and impurities are accumulated in the reaction mother liquor as the number of cycles of performing the reaction increases, and when the concentration of such impurities exceeds a prescribed value, they are precipitated in the spiroglycol, resulting in lowering the purity of the spiroglycol to be obtained.

Also in the crystallization step using an organic solvent, the crystallization mother liquor may be similarly reused in the crystallization of the next cycle, but impurities are accumulated in the crystallization mother liquor as the number of reuses increases, and when the concentration of the impurities exceeds a prescribed value, they are precipitated in the product of a spiroglycol, and hence a high purity spiroglycol cannot be obtained.

This problem can similarly apply to a diol having a cyclic acetal skeleton such as dioxane glycol.

The present invention was devised in consideration of these problems, and another object is to provide a method for producing a diol having a cyclic acetal skeleton capable of industrially advantageously producing a high purity diol having a cyclic acetal skeleton even when a reaction mother liquor is repeatedly used.

Solution to Problem

The present inventors made earnest studies to solve the above-described problems. As a result, they have found that impurities contained in HPA used as a raw material of a diol having a cyclic acetal skeleton affect impurities contained in the diol having a cyclic acetal skeleton obtained by a synthesis reaction, and found that the above-described problems can be solved by controlling the amount of impurities contained in the raw material HPA, resulting in accomplishing the present invention.

Specifically, the present invention provides:

[1]

A method for producing a diol having a cyclic acetal skeleton, comprising:

an acetalization reaction step of subjecting raw material hydroxypivalaldehyde and at least pentaerythritol and/or trimethylolpropane to an acetalization reaction under an acid catalyst to obtain a diol having a cyclic acetal skeleton, wherein the raw material hydroxypivalaldehyde comprises at least one impurity selected from the group consisting of formaldehyde, neopentyl glycol, an ester compound having a neopentyl glycol skeleton represented by following formula (III), and isobutyraldehyde, wherein R represents a hydrocarbon group having 1 to 4 carbon atoms, a hydrocarbon group having a hydroxy group and having 1 to 4 carbon atoms, or a hydrogen atom, and when the impurity is comprised, a content of the formaldehyde is 0.80% by mass or less based on 100% by mass of the raw material hydroxypivalaldehyde; a total molar concentration of the neopentyl glycol and/or the ester compound having a neopentyl glycol skeleton is 0.100 mol/kg or less based on a total amount of the raw material hydroxypivalaldehyde; and a content of the isobutyraldehyde is 0.05% by mass or less based on 100% by mass of the raw material hydroxypivalaldehyde.

[2]

The method for producing the diol having the cyclic acetal skeleton according to [1], wherein in terms of an area fractional concentration based on a sum of components having a relative retention time of 1.45 or less on the assumption that a relative retention time of the diol having a cyclic acetal skeleton in gas chromatography analysis performed under prescribed conditions is 1.00, the diol having a cyclic acetal skeleton obtained by the acetalization reaction comprises, as an impurity, a dioxane triol monoformal represented by following formula (I) in an amount of 0.04 area % or less:

[3]

The method for producing the diol having the cyclic acetal skeleton according to [1] or [2], wherein in terms of an area fractional concentration based on a sum of components having a relative retention time of 1.45 or less on the assumption that a relative retention time of the diol having a cyclic acetal skeleton in gas chromatography analysis performed under prescribed conditions is 1.00, the diol having a cyclic acetal skeleton obtained by the acetalization reaction comprises, as an impurity, a hydroxypivalaldehyde neopentyl glycol acetal represented by following formula (II) in an amount of 0.19 area % or less:

[4]

The method for producing the diol having the cyclic acetal skeleton according to any one of [1] to [3], wherein in terms of an area fractional concentration based on a sum of components having a relative retention time of 1.45 or less on the assumption that a relative retention time of the diol having a cyclic acetal skeleton in gas chromatography analysis performed under prescribed conditions is 1.00, the diol having a cyclic acetal skeleton obtained by the acetalization reaction comprises, as an impurity, a spiro monoalcohol represented by following formula (IV) in an amount of 0.15 area % or less:

(IV)

[5]

The method for producing the diol having the cyclic acetal skeleton according to any one of [1] to [4], wherein the ester compound represented by the formula (III) comprises an isobutyric acid neopentyl glycol monoester represented by following formula (V) and/or a hydroxypivalic acid neopentyl glycol monoester represented by following formula (VI):

(V)

(VI)

[6]

The method for producing the diol having the cyclic acetal skeleton according to any one of [1] to [5], wherein the diol having a cyclic acetal skeleton is spiroglycol and/or dioxane glycol.

[7]

The method for producing the diol having the cyclic acetal skeleton according to any one of [1] to [6], comprising an aldol condensation reaction step of obtaining crude hydroxypivalaldehyde by an aldol condensation reaction of formaldehyde and isobutyraldehyde.

[8]

The method for producing the diol having the cyclic acetal skeleton according to [7], comprising at least any one of:

an extraction step of adding water and/or an organic solvent to crude hydroxypivalaldehyde obtained in the aldol condensation reaction step to extract the raw material hydroxypivalaldehyde;

a distillation step of distilling the crude hydroxypivalaldehyde obtained in the aldol condensation reaction step to collect the raw material hydroxypivalaldehyde as a distillate; and a crystallization step of adding water and/or an organic solvent to the crude hydroxypivalaldehyde obtained in the aldol condensation reaction step for crystallization and collecting the raw material hydroxypivalaldehyde by solid-liquid separation.

[9]

The method for producing the diol having the cyclic acetal skeleton according to any one of [1] to [8], wherein a reaction temperature employed in the acetalization reaction step is 40 to 105° C., a pH value of a reaction solution in the acetalization reaction step is 0.1 to 4.0, and after the acetalization reaction step, the reaction solution is solid-liquid separated into a solid of the diol having the cyclic acetal skeleton and a reaction mother liquor after the acetalization reaction step, and 30 to 98% by mass of the reaction mother liquor is reused to perform a subsequent acetalization reaction step.

Advantageous Effects of Invention

According to the present invention, a method for producing the diol having the cyclic acetal skeleton capable of producing a high purity diol having a cyclic acetal skeleton, and a method for producing the diol having the cyclic acetal skeleton capable of industrially advantageously producing a high purity diol having a cyclic acetal skeleton even when a reaction mother liquor is repeatedly used can be provided. Besides, the high purity diol having a cyclic acetal skeleton thus obtained can be industrially advantageously used mainly as a resin raw material.

DESCRIPTION OF EMBODIMENT

Now, an embodiment for carrying out the present invention (hereinafter referred to as the "present embodiment") will be described in detail, and it is noted that the present invention is not limited to this embodiment but may be variously modified and changed without departing from the purport thereof.

[Method for Producing Diol Having Cyclic Acetal Skeleton]

A method for producing a diol having a cyclic acetal skeleton of the present embodiment comprises an acetalization reaction step of subjecting raw material hydroxypivalaldehyde (hereinafter also referred to as the "raw material HPA") and at least pentaerythritol and/or trimethylolpropane to an acetalization reaction under an acid catalyst to obtain the diol having the cyclic acetal skeleton, the raw material hydroxypivalaldehyde comprises at least one impurity selected from the group consisting of formaldehyde, neopentyl glycol, an ester compound having a neopentyl glycol skeleton represented by following formula (III), and isobutyraldehyde:

(III)

wherein R represents a hydrocarbon group having 1 to 4 carbon atoms, a hydrocarbon group having a hydroxy group and having 1 to 4 carbon atoms, or a hydrogen atom, and when the impurity is comprised, a content of the formaldehyde is 0.80% by mass or less based on 100% by mass of the raw material hydroxypivalaldehyde, a total molar concentration of the neopentyl glycol and/or the ester compound having a neopentyl glycol skeleton is 0.100 mol/kg or less based on a total amount of the raw material hydroxypivalaldehyde, and a content of the isobutyraldehyde is 0.05% by mass or less based on 100% by mass of the raw material hydroxypivalaldehyde.

In the method for producing the diol having the cyclic acetal skeleton of the present embodiment, the contents of the formaldehyde, the neopentyl glycol, the ester compound having a neopentyl glycol skeleton and the isobutyraldehyde corresponding to the impurities contained in the raw material HPA are controlled so as to inhibit generation of various acetal compounds corresponding to by-products in synthesis of the diol having a cyclic acetal skeleton, and thus, a high purity diol having a cyclic acetal skeleton can be obtained. Besides, the diol having a cyclic acetal skeleton to be produced in the present embodiment is not especially limited, and examples thereof include a spiroglycol and/or a dioxane glycol. Incidentally, the spiroglycol is a compound represented by following formula (A), and the dioxane glycol is a compound represented by following formula (B):

The raw material HPA may comprise, but preferably does not comprise, a prescribed amount of formaldehyde as an impurity. A content of the formaldehyde that can be contained in the raw material HPA is 0.80% by mass or less, preferably 0.55% by mass or less, and more preferably 0.35% by mass or less based on 100% by mass of the raw material HPA. The lower limit of the content of the formaldehyde that can be contained in the raw material HPA is not especially limited, and is preferably below the detection limit or 0% by mass. The content of the formaldehyde that can be contained in the raw material HPA can be measured by acetylacetone colorimetry, and more specifically, can be measured by a method described in an example below. Besides, the content of the formaldehyde that can be contained in the raw material HPA can be reduced by purification of the raw material HPA described later.

The raw material HPA may comprise, but preferably does not comprise, a prescribed amount of neopentyl glycol and/or an ester compound having a neopentyl glycol skeleton represented by formula (III) as an impurity. The ester compound represented by formula (III) is not especially limited, and specific examples thereof include an isobutyric acid neopentyl glycol monoester represented by following formula (V) and/or a hydroxypivalic acid neopentyl glycol monoester represented by following formula (VI):

wherein R represents a hydrocarbon group having 1 to 4 carbon atoms, a hydrocarbon group having a hydroxy group and having 1 to 4 carbon atoms, or a hydrogen atom.

A total content of the neopentyl glycol and/or the ester compound having a neopentyl glycol skeleton represented by formula (III) that can be contained in the raw material HPA is, in terms of molar concentration, 0.100 mol/kg or less, preferably 0.080 mol/kg or less, and more preferably 0.060 mol/kg or less. The lower limit of the content of the neopentyl glycol and/or the ester compound having a neopentyl glycol skeleton represented by formula (III) that can be contained in the raw material HPA is not especially limited, and is preferably below the detection limit or 0 mol/kg. The content of the neopentyl glycol and/or the ester compound having a neopentyl glycol skeleton represented by formula (III) that can be contained in the raw material HPA can be measured by gas chromatography, and more specifically, can be measured by a method described in an example below. Besides, the content of the neopentyl glycol and/or the ester compound having a neopentyl glycol skeleton represented by formula (III) that can be contained in the raw material HPA can be reduced by the purification of the raw material HPA described later.

The raw material HPA may comprise, but preferably does not comprise, a prescribed amount of isobutyraldehyde as an impurity. A total content of the isobutyraldehyde that can be contained in the raw material HPA is 0.10% by mass or less, preferably 0.07% by mass or less, and more preferably 0.05% by mass or less based on 100% by mass of the raw material HPA. The lower limit of the content of the isobutyraldehyde that can be contained in the raw material HPA is not especially limited, and is preferably below the detection limit or 0% by mass. The content of the isobutyraldehyde that can be contained in the raw material HPA can be measured by the gas chromatography, and more specifically, can be measured by a method described in an example below. Besides, the content of the isobutyraldehyde that can be contained in the raw material HPA can be reduced by the purification of the raw material HPA described later.

The diol having the cyclic acetal skeleton obtained by an acetalization reaction may comprise, but preferably does not comprise, a dioxane triol monoformal represented by formula (I) as an impurity.

(I)

A content of the dioxane triol monoformal can be expressed as an area fractional concentration obtained on the assumption that a relative retention time of the diol having a cyclic acetal skeleton in gas chromatography analysis performed under prescribed conditions is 1.00 and that components having a relative retention time of 1.45 or less are summed up as 100 area %. In this case, the content of the dioxane triol monoformal is 0.04 area % or less, preferably 0.03 area % or less, and more preferably 0.02 area % or less. The lower limit of the content of the dioxane triol monoformal is not especially limited, and is preferably below the detection limit or 0 area %. The content of the dioxane triol monoformal can be measured by the gas chromatography, and more specifically, can be measured by a method described in an example below. Besides, the content of the dioxane triol monoformal that can be contained in the diol having a cyclic acetal skeleton obtained by the acetalization reaction can be reduced by reducing the formaldehyde contained in the raw material HPA described later. It is noted that the term "prescribed conditions" herein means that the measurement is performed under the following conditions on the assumption that a relative retention time of the diol having a cyclic acetal skeleton is 1.00, and that a total area in a GC chart of components, excluding methanol, having a relative retention time of 1.45 or less is 100 area %.

(Conditions)

Measurement sample: prepared in the form of a 2.5% by mass methanol solution

Apparatus: GC-1700 (manufactured by Shimadzu Corporation)

Column used: DB-1 having a length of 30 m×an inner diameter of 0.53 mm, and a film thickness of 1.5 µm (manufactured by Agilent Technologies Japan, Ltd.)

Analysis conditions: injection temperature: 280° C.

detection temperature: 280° C.

Carrier gas: helium

Column temperature: A temperature of 80° C. is kept for 4 minutes, the temperature is increased to 250° C. at 6° C./min, the temperature of 250° C. is kept for 10 minutes, the temperature is increased to 280° C. at 10° C./min, and the temperature of 280° C. is kept for 15 minutes.

Detector: flame ionization detector (FID)

The diol having a cyclic acetal skeleton obtained by the acetalization reaction may comprise, but preferably does not comprise, a hydroxypivalaldehyde neopentyl glycol acetal represented by formula (II) as an impurity.

(II)

A content of the hydroxypivalaldehyde neopentyl glycol acetal can be expressed as an area fractional concentration obtained on the assumption that a relative retention time of the diol having a cyclic acetal skeleton in the gas chromatography analysis performed under the prescribed conditions is 1.00 and that components having a relative retention time of 1.45 or less are summed up as 100 area %. In this case, the content of the hydroxypivalaldehyde neopentyl glycol acetal is 0.19 area % or less, preferably 0.13 area % or less, and more preferably 0.08 area % or less. The lower limit of the content of the hydroxypivalaldehyde neopentyl glycol acetal is not especially limited, and is preferably below the detection limit or 0 area %. The content of the hydroxypivalaldehyde neopentyl glycol acetal can be measured by the gas chromatography, and more specifically, can be measured by a method described in an example below. Besides, the content of the hydroxypivalaldehyde neopentyl glycol acetal that can be contained in the diol having a cyclic acetal skeleton obtained by the acetalization reaction can be reduced by reducing the neopentyl glycol and/or the ester compound having a neopentyl glycol skeleton represented by formula (III) contained in the raw material HPA.

The diol having a cyclic acetal skeleton obtained by the acetalization reaction may comprise, but preferably does not comprise, a spiro monoalcohol represented by formula (IV) as an impurity.

(IV)

A content of the spiro monoalcohol can be expressed as an area fractional concentration obtained on the assumption that a relative retention time of the diol having a cyclic acetal skeleton in the gas chromatography analysis performed under the prescribed conditions is 1.00 and that components having a relative retention time of 1.45 or less are summed up as 100 area %. In this case, the content of the spiro monoalcohol is 0.15 area % or less, preferably 0.13 area % or less, and more preferably 0.12 area % or less. The lower limit of the content of the spiro monoalcohol is not especially limited, and is preferably below the detection limit or 0 area %. The content of the spiro monoalcohol can be measured by the gas chromatography, and more specifically, can be measured by a method described in an example below. Besides, the content of the spiro monoalcohol that can be contained in the diol having a cyclic acetal skeleton obtained by the acetalization reaction can be reduced by reducing the isobutyraldehyde contained in the raw material HPA.

[Aldol Condensation Reaction Step]

The production method of the present embodiment may comprise an aldol condensation reaction step of synthesizing the raw material HPA used as a raw material of the diol having a cyclic acetal skeleton. The aldol condensation reaction step is a step of obtaining a crude hydroxypivalaldehyde (hereinafter also referred to as the "crude HPA") by an aldol condensation reaction of formaldehyde and isobutyraldehyde. In the aldol condensation reaction step, a basic catalyst may be used, if necessary. Besides, the formaldehyde includes a formaldehyde aqueous solution (formalin). It is noted that the crude HPA may comprise impurities as those contained in the raw material HPA.

The basic catalyst used in the aldol condensation reaction step is not especially limited, and examples thereof include inorganic bases such as sodium hydroxide, potassium hydroxide, sodium carbonate and potassium carbonate; and organic bases such as a tertiary amine and pyridine. Among these, a tertiary amine is preferred. When such a basic catalyst is used, there is a tendency that the reduction of HPA yield otherwise caused because of Cannizzaro reaction of HPA with unreacted formaldehyde also caused due to too strong basicity is inhibited, and that the reduction of reaction rate otherwise caused because of too week basicity is inhibited.

The tertiary amine is not especially limited, and examples thereof include trimethylamine, triethylamine, tripropylamine, triisopropylamine, tributylamine, triisobutylamine, N-methylpiperidine, N-ethylpiperidine, N-methylmorpholine, N-ethylmorpholine, N-methylpyrrolidine and N-ethylpyrrolidine. Among these, trimethylamine and triethylamine inexpensively available are preferred, and triethylamine is more preferred.

An amount of the basic catalyst to be used is naturally varied depending on the type of the basic catalyst, and is preferably 0.001 to 0.5 mol, and more preferably 0.01 to 0.2 mol per mol of isobutyraldehyde.

[Crude Hydroxypivalaldehyde Purification Step]

The production method of the present embodiment may comprise a crude hydroxypivalaldehyde purification step of obtaining the raw material HPA by purifying the crude hydroxypivalaldehyde obtained in the aldol condensation reaction step. The crude HPA purification step is not especially limited, and can be, for example, an extraction step of adding water and/or an organic solvent to the crude HPA obtained in the aldol condensation reaction step to extract the raw material HPA; a distillation step of distilling the crude HPA obtained in the aldol condensation reaction step to collect the raw material HPA as a distillate; and a crystallization step of adding water and/or an organic solvent to the crude HPA obtained in the aldol condensation reaction step for crystallization and collecting the raw material HPA by solid-liquid separation. Single one of these steps may be performed, or two or more of these may be performed together.

(Extraction Step)

The organic solvent used in the extraction step is not especially limited, and an example thereof includes isobutyraldehyde. In the extraction step, the raw material HPA is extracted in an isobutyraldehyde layer.

(Distillation Step)

Distillation conditions for the crude HPA are not especially limited, and for example, a column top temperature can be 88 to 150° C. and a column top absolute pressure can be 1.0 kPa to 1 MPa.

(Crystallization Step)

The organic solvent used in the crystallization step is not especially limited, and an example thereof includes water. Besides, a solid-liquid separation method is not especially limited, and for example, any of known methods such as filtration and centrifugation can be employed. A temperature to be controlled as a condition for the crystallization is not especially limited, and can be 10 to 80° C.

In the crude hydroxypivalaldehyde purification step, the purification is performed preferably so that a content of formaldehyde in the raw material HPA can be 0.80% by mass or less based on 100% by mass of the raw material HPA. If the content of the formaldehyde in the raw material HPA exceeds 0.80% by mass, acetalization is caused in HPA, PE and formaldehyde during the synthesis reaction of the diol having a cyclic acetal skeleton (the acetalization reaction step), and hence the amount of 2-methyl-2-(2,4,8,10-tetraoxaspiro[5.5]undecane-3-yl)propane-1-ol (hereinafter also referred to as "dioxane triol monoformal") to be produced as a by-product increases. If there is a prescribed or larger amount of dioxane triol monoformal, it is easily mixed into the crystals of the diol having a cyclic acetal skeleton, resulting in lowering the purity of the resultant diol having a cyclic acetal skeleton.

Besides, in the crude hydroxypivalaldehyde purification step, the purification is performed preferably so that a sum of molarities of neopentyl glycol and an ester compound having a neopentyl glycol skeleton, such as 3-hydroxy-2,2-dimethylpropyl 2-methylpropanoate (hereinafter also referred to as "isobutyric acid neopentyl glycol monoester") or 3-hydroxy-2,2-dimethylpropyl 3-hydroxy-2,2-dimethylpropanoate (hereinafter also referred to as "hydroxypivalic acid neopentyl glycol monoester"), contained in the raw material HPA can be 0.100 mol/kg or less. If the ester compound having a neopentyl glycol skeleton contained in the raw material HPA exceeds 0.100 mol/kg, the ester compound is hydrolyzed during the synthesis reaction of the diol having a cyclic acetal skeleton (the acetalization reaction step) to generate neopentyl glycol, acetalization is caused between the neopentyl glycol and the HPA, and hence an amount of 2-methyl-2-(5,5-dimethyl-1,3-dioxane-2-yl)-1-propanol (hereinafter also referred to as "hydroxypivalaldehyde neopentyl glycol acetal") to be produced as a by-product increases. If there is a prescribed or larger amount of hydroxypivalaldehyde neopentyl glycol acetal, it is easily mixed into the crystals of the diol having a cyclic acetal skeleton, resulting in lowering the purity of the resultant diol having a cyclic acetal skeleton.

Besides, in the crude hydroxypivalaldehyde purification step, the purification is performed preferably so that a content of isobutyraldehyde in the raw material HPA can be 0.05% by mass or less based on 100% by mass of the raw material HPA. If the isobutyraldehyde contained in the raw material HPA exceeds 0.05% by mass, acetalization is caused in the isobutyraldehyde, the HPA and the PE during the synthesis of the diol having a cyclic acetal skeleton (the acetalization reaction step), and hence an amount of 2-methyl-2-(9-propane-2-yl-2,4,8,10-tetraoxaspiro[5.5]undecane-3-yl)propane-1-ol (hereinafter also referred to as "spiro monoalcohol") to be produced as a by-product is increased. If there is a prescribed or larger amount of spiro monoalcohol, it is easily mixed into the crystals of the diol having a cyclic acetal skeleton, resulting in lowering the purity of the resultant diol having a cyclic acetal skeleton.

There is a tendency that the dioxane triol monoformal, the hydroxypivalaldehyde neopentyl glycol acetal and the spiro monoalcohol are easily incorporated into the crystals of the diol having a cyclic acetal skeleton during the synthesis reaction of the diol having a cyclic acetal skeleton performed in a water solvent, or are easily incorporated in a comparatively large amount into a product of the diol having a cyclic acetal skeleton because they have low solubility in the reaction mother liquor.

[Acetalization Reaction Step]

The acetalization reaction step is a step of obtaining the diol having a cyclic acetal skeleton by causing, under an acid catalyst, an acetalization reaction between the raw material HPA and PE. In the acetalization reaction step, a molar ratio of the raw material HPA to the PE (HPA/PE) is preferably 1.0 to 4.0, and more preferably 1.5 to 2.5. When the molar ratio (HPA/PE) is 4.0 or less, an amount of an excessive portion of the raw material HPA not involved in the reaction is reduced to inhibit a side reaction such as dimerization of the HPA, and therefore, there is a tendency that the degradation of specific consumption and degradation of purity of the diol having a cyclic acetal skeleton can be inhibited. On the other hand, when the molar ratio (HPA/PE) is 1.0 or more, degradation of the yield of the diol having a cyclic acetal skeleton due to production of a large amount of a reaction intermediate of the diol having a cyclic acetal skeleton can be inhibited, and there is a tendency that the degradation of the purity of the diol having a cyclic acetal skeleton otherwise caused by the intermediate and the degradation of the specific consumption of the PE can be inhibited.

In the acetalization reaction step, a solvent can be used, if necessary. The solvent is not especially limited, and for example, water can be used.

In the production method of the present embodiment, a seed crystal may be added to the reaction system, if necessary. As the seed crystal, crystals mainly of the diol having the cyclic acetal skeleton are used. The size of the seed crystal is not especially limited, and is preferably 5 μm or more, and more preferably 10 μm or more. An addition amount of the seed crystal is preferably 1.5 to 30% by mass, and more preferably 1.5 to 5% by mass based on the total supply amount (of the raw material, the solvent, the catalyst and the seed crystal) to the reaction system. When the addition amount of the seed crystal is 1.5% by mass or more, an effect to improve the crystal size is more efficiently exhibited, and hence, there is a tendency that a filtration time of the crystals of the resultant diol having a cyclic acetal skeleton can be shortened or a cake is difficult to be cracked during the filtration and washability is more improved, and that a liquid content of the wet cake is lowered. On the other hand, when it is larger than this range, an amount of the crystals obtained through the reaction is reduced, and hence the production efficiency of the diol having a cyclic acetal skeleton is degraded. It is noted that the seed crystal may be added before or during the reaction.

The acid catalyst used in the reaction is not especially limited, and examples thereof include mineral acids such as hydrochloric acid, sulfuric acid, phosphoric acid and nitric acid, or organic acids such as para-toluenesulfonic acid and methanesulfonic acid. At this point, an amount of the acid catalyst to be used is varied depending on the type of the acid catalyst, and is generally set so that a pH value of the reaction solution during the reaction can be preferably 0.1 to 4.0, and more preferably 1.0 to 2.0. When the pH value is 0.1 or more, a risk of corrosion of a used device and the like tends to be further reduced. Besides, when the pH value is 4.0 or less, the reactivity is further improved, and the yield of the diol having a cyclic acetal skeleton tends to be further improved.

A reaction temperature of the acetalization reaction is preferably 40 to 105° C., and more preferably 60 to 95° C. When the reaction temperature is 40° C. or more, there is a tendency that a reaction time is industrially advantageously shortened. Besides, when the reaction temperature is 105° C. or less, quality change of HPA is inhibited, and hence the yield and the purity of the diol having a cyclic acetal skeleton tend to be further improved.

A method for the acetalization reaction may be a batch method, a semi-batch method or a continuous method, or these methods may be combined. In employing the batch method, raw materials excluding the raw material HPA are charged in a reactor, the resultant is heated to a prescribed temperature, and then the raw material HPA or an aqueous solution thereof is continuously added thereto over 0.5 to 24 hours, and preferably 1 to 6 hours. The diol having a cyclic acetal skeleton is precipitated during the synthesis reaction, and the reaction solution is in the form of slurry. When the addition time is short (namely, a large amount is added in a short time), the reaction proceeds so rapidly that the size of the resultant crystals tends to be small. The addition time preferably falls in the above-described range from the industrial point of view because the purity of the diol having a cyclic acetal skeleton is further increased, and the time required for the reaction can be shortened.

[Separation/Purification Step of Diol Having Cyclic Acetal Skeleton]

The production method of the present embodiment may comprise a separation/purification step of the diol having a cyclic acetal skeleton of separating the diol having a cyclic acetal skeleton precipitated in the reaction solution and washing the thus separated diol having a cyclic acetal skeleton. The reaction solution obtained through the above-described reaction is in the form of slurry in which the diol having a cyclic acetal skeleton of interest is precipitated, and the crystals of the diol having a cyclic acetal skeleton can be separated therefrom by filtration, centrifugation or the like. The diol having a cyclic acetal skeleton separated by the filtration is washed with a basic aqueous solution and/or water.

An amount of the wash water to be used is preferably 0.1 to 10 times, and more preferably 0.5 to 3 times as much as the weight of the separated liquid-containing diol having a cyclic acetal skeleton. A washing liquid recovered through the washing can be used in the reaction of the next cycle directly or after being mixed with the reaction mother liquor.

The type of a base of the basic aqueous solution is not especially limited, and examples thereof include, inorganic bases such as lithium carbonate, lithium hydrogen carbonate, magnesium carbonate, sodium hydrogen carbonate, potassium hydrogen carbonate, sodium carbonate, potassium carbonate, sodium hydroxide, potassium hydroxide, sodium phosphate, potassium phosphate, calcium carbonate, calcium hydroxide and barium carbonate, and organic bases such as diethylamine and triethylamine. Among these, an inorganic base is preferably used from the viewpoints of physical properties, coloring, odor and the like of a derivative to be synthesized using the diol having a cyclic acetal skeleton.

Here, the reaction mother liquor obtained by separating the crystals of the diol having a cyclic acetal skeleton from the reaction solution contains large amounts of the acid catalyst, unreacted HPA and PE, and a reaction intermediate. In the present embodiment, after the acetalization reaction step, the reaction solution is solid-liquid separated into the solid of the diol having a cyclic acetal skeleton and the reaction mother liquor, and 30 to 98% by mass of the reaction mother liquor can be reused in the acetalization reaction step of the next cycle.

An amount of the reaction mother liquor to be reused is preferably 30 to 98% by mass, and more preferably 50 to 90% by mass based on a total amount of the reaction mother liquor. When a reused ratio is 98% by mass or less, impurities are difficult to be accumulated in the mother liquor, and hence there is a tendency that the precipitation of impurities in the diol having a cyclic acetal skeleton can be more inhibited.

[Polyester Resin]

A polyester resin of the present embodiment comprise a diol constituting unit and a dicarboxylic acid constituting unit, and the diol constituting unit contains a constituting unit derived from the diol having the cyclic acetal skeleton represented by following formula (A) and/or formula (B):

-continued (B)

[Diol Constituting Unit]

The diol constituting unit comprises the constituting unit derived from the diol having a cyclic acetal skeleton represented by formula (A) and/or formula (B), and may comprise a constituting unit derived from an additional diol, if necessary.

A content of the constituting unit derived from the diol having a cyclic acetal skeleton is preferably 1 to 80% by mol, more preferably 3 to 60% by mol, further preferably 5 to 55% by mol, and particularly preferably 10 to 50% by mol based on a total amount of the diol constituting unit.

(Additional Diol)

The additional diol is not especially limited, and examples thereof include aliphatic diols such as ethylene glycol, trimethylene glycol, 1,4-butanediol, 1,5-pentanediol, 1,6-hexanediol, diethylene glycol, propylene glycol and neopentyl glycol; polyether diols such as polyethylene glycol, polypropylene glycol and polybutylene glycol; alicyclic diols such as 1,3-cyclohexanedimethanol, 1,4-cyclohexandimethanol, 1,2-decahydronaphthalenedimethanol, 1,3-decahydronaphthalenedimethanol, 1,4-decahydronaphthalenedimethanol, 1,5-decahydronaphthalenedimethanol, 1,6-decahydronaphthalenedimethanol, 2,7-decahydronaphthalenedimethanol, tetralin dimethanol, norbornane dimethanol, tricyclodecane dimethanol and pentacyclododecane dimethanol; bisphenols such as 4,4'-(1-methylethylidene)bisphenol, methylene bisphenol (also called as bisphenol F), 4,4'-cyclohexylidene bisphenol (also called as bisphenol Z) and 4,4'-sulfonyl bisphenol (also called as bisphenol S); alkylene oxide adducts of these bisphenols; aromatic dihydroxy compounds such as hydroquinone, resorcin, 4,4'-dihydroxybiphenyl, 4,4'-dihydroxydiphenyl ether and 4,4'-dihydroxydiphenyl benzophenone; and alkylene oxide adducts of these aromatic dihydroxy compounds.

Among these, from the viewpoints of mechanical properties, economical properties and the like of the polyester resin, ethylene glycol, diethylene glycol, trimethylene glycol, 1,4-butanediol and 1,4-cyclohexanedimethanol are preferred, and ethylene glycol is particularly preferred. One of these additional diols may be singly used, or two or more of these may be used together.

A content of the constituting unit derived from the additional diol is 20 to 99% by mol, preferably 40 to 97% by mol, more preferably 45 to 95% by mol and further preferably 50 to 90% by mol based on the total amount of the diol constituting unit.

[Dicarboxylic Acid Constituting Unit]

The dicarboxylic acid constituting unit is not especially limited, and examples thereof include aliphatic dicarboxylic acids such as succinic acid, glutaric acid, adipic acid, pimelic acid, suberic acid, azelaic acid, sebacic acid, dodecanedicarboxylic acid, cyclohexanedicarboxylic acid, decanedicarboxylic acid, norbornanedicarboxylic acid, tricyclodecanedicarboxylic acid and pentacyclododecanedicarboxylic acid; and aromatic dicarboxylic acids such as terephthalic acid, isophthalic acid, phthalic acid, 2-methyl terephthalic acid, 1,4-naphthalenedicarboxylic acid, 1,5-naphthalenedicarboxylic acid, 2,6-naphthalenedicarboxylic acid, 2,7-naphthalenedicarboxylic acid, biphenyldicarboxylic acid and tetralindicarboxylic acid. Among these, from the viewpoints of mechanical properties and heat resistance of the polyester resin, aromatic dicarboxylic acids, such as terephthalic acid, isophthalic acid, 1,4-naphthalenedicarboxylic acid, 1,5-naphthalenedicarboxylic acid, 2,6-naphthalenedicarboxylic acid and 2,7-naphthalenedicarboxylic acid are preferred, and terephthalic acid, 2,6-naphthalenedicarboxylic acid and isophthalic acid are particularly preferred. In particular, terephthalic acid is most preferred from the viewpoint of economical property. One of these dicarboxylic acids may be singly used, or two or more of these may be used together.

[Method for Producing Polyester Resin]

A method for producing the polyester resin is not especially limited, and any of known methods can be applied. Examples thereof include melt polymerization methods such as a transesterification method and a direct esterification method, and a solution polymerization method. A raw material purified as described above is preferably used.

In each of the above-described methods, a known catalyst can be used. The known catalyst is not especially limited, and examples thereof include alkoxides of metal magnesium, sodium and magnesium; and fatty acid salts, carbonates, hydroxides, chlorides and oxides of zinc, lead, cerium, cadmium, manganese, cobalt, lithium, sodium, potassium, calcium, nickel, magnesium, vanadium, aluminum, tin, germanium, antimony and titanium. Among these, compounds of manganese, titanium, antimony and germanium are preferred, and manganese acetate, tetrabutoxy titanium, antimony trioxide and germanium dioxide are particularly preferred. One of these catalysts may be singly used, or two or more of these may be used together.

In each of the above-described methods, a known additive may be used, if necessary. The known additive is not especially limited, and examples thereof include an anti-etherifying agent, various stabilizers such as a heat stabilizer and a light stabilizer, a polymerization modifier, an antistatic agent, a lubricant, an antioxidant, a release agent and a basic compound.

The anti-etherifying agent is not especially limited, and examples thereof include amine compounds.

The heat stabilizer is not especially limited, and examples thereof include phosphorus compounds. Among the compounds, phosphoric acid esters are preferred, and triethyl phosphate is more preferred.

The basic compound is not especially limited, and examples thereof include carbonates, hydroxides, carboxylates, oxides, chlorides and alkoxides of alkali metals such as lithium, sodium and potassium. Among these, potassium acetate, sodium acetate and lithium acetate are particularly preferred.

[Use]

The polyester resin of the present embodiment can be applied to various uses. For example, it can be used in an injection molded article, a sheet, a film, an extrusion molded article such as a pipe, a bottle, a foaming material, an adhesive material, an adhesive, a paint and the like. More specifically, the sheet may be a single-layered or multilayered sheet, the film may be a single-layered or multilayered film, or may be unstretched or one-way or two-way stretched, and may be stacked on a steel plate or the like. The bottle may be a direct blow bottle or an injection blow bottle, or may be injection molded. The foaming material may be a bead foaming material or an injection foaming material.

EXAMPLES

Next, the present invention will be described more specifically. It is noted that the present invention is not limited to the following description.

[Conditions of Gas Chromatography Analysis of Diol Having Cyclic Acetal Skeleton]

The purity analysis of an obtained diol having a cyclic acetal skeleton was performed by the gas chromatography under the following conditions. Assuming that a relative retention time of the diol having a cyclic acetal skeleton was 1.00 and that a total area in a GC chart of components, excluding methanol, having a relative retention time of 1.45 or less was 100 area %, an area fractional concentration of each component was obtained.

(Conditions)

Measurement sample: prepared in the form of a 2.5% by mass methanol solution

Apparatus: GC-1700 (manufactured by Shimadzu Corporation)

Column used: DB-1 having a length of 30 m×an inner diameter of 0.53 mm, and a film thickness of 1.5 μm (manufactured by Agilent Technologies Japan, Ltd.)

Analysis conditions: injection temperature: 280° C.
detection temperature: 280° C.
Carrier gas: helium
Column temperature: A temperature of 80° C. was kept for 4 minutes, the temperature was increased to 250° C. at 6° C./min, the temperature of 250° C. was kept for 10 minutes, the temperature was increased to 280° C. at 10° C./min, and the temperature of 280° C. was kept for 15 minutes.

Detector: flame ionization detector (FID)

[Conditions of Analysis of HPA]

The purities of crude HPA and purified HPA obtained as described below were measured by the gas chromatography analysis and a formaldehyde determination method performed under the following conditions:

(Conditions of Gas Chromatography Analysis)

Measurement sample: prepared in the form of a 1% by mass acetone solution

Apparatus: GC-6890N (manufactured by Agilent Technologies Japan, Ltd.)

Column used: DB-1 having a length of 30 m×an inner diameter of 0.53 mm, and a film thickness of 1.5 μm (manufactured by Agilent Technologies Japan, Ltd.)

Analysis conditions: injection temperature: 200° C.
detection temperature: 250° C.
Carrier gas: helium
Column temperature: A temperature of 60° C. was kept for 7 minutes, the temperature was increased to 250° C. at 6° C./min, and the temperature of 250° C. was kept for 20 minutes.

Detector: flame ionization detector (FID)

(Formaldehyde Determination)

The measurement was performed by the acetylacetone colorimetry using a UV spectrometer.

<Production Example 1> (Preparation of Crude HPA Aqueous Solution)

200 parts by mass of isobutyraldehyde (a product of Wako Pure Chemical Industries Ltd.) and 225 parts by mass of 40% by mass formalin (a product of Mitsubishi Gas Chemical Company, Inc.) were charged to perform an aldol condensation reaction, under stirring at 40° C. in a nitrogen stream, by adding 9.9 parts by mass of triethylamine (a product of Wako Pure Chemical Industries Ltd.) as a catalyst thereto over 5 minutes. After completing the addition of triethylamine, the temperature of the resultant reaction solution reached 65° C. From this temperature, the temperature of the reaction solution was gradually increased, and the temperature of the reaction solution was set to 90° C. after 30 minutes. After the reaction was continued for 50 minutes at the temperature of the reaction solution of 90° C., the temperature of the reaction solution was lowered to 60° C. by external cooling, and the reaction was stopped.

Subsequently, under conditions of 70 to 80° C. and a pressure of 40 kPa, unreacted portions of isobutyraldehyde and triethylamine and a low boiling point component such as methanol were distilled off from the reaction solution, and thus, 425 parts by mass of a crude HPA aqueous solution was obtained. The composition of the crude HPA aqueous solution was analyzed by the gas chromatography (manufactured by Agilent Technologies Japan, Ltd.). As a result, the crude HPA aqueous solution was found to contain 62.5% by mass of HPA, 0.30% by mass of isobutyraldehyde, 1.17% by mass of neopentyl glycol, 1.55% by mass of formaldehyde, 1.29% by mass of triethylamine, 0.38% by mass of formic acid, 0.85% by mass of hydroxypivalic acid neopentyl glycol monoester, 0.15% by mass of isobutyric acid neopentyl glycol monoester, 30.52% by mass of water and 1.29% by mass of other components.

<Production Example 2> (Preparation of Purified HPA)

A crystallization tank was charged with 260 parts by mass of the crude HPA aqueous solution obtained in Production Example 1 and 590 parts by mass of water, the concentration of HPA was set to 19.0% by mass and the resultant solution was kept at 60° C. This solution was cooled to 40° C. under stirring and kept at 39 to 40° C. After 90 minutes, resultant whole slurry containing crystals of HPA was solid-liquid separated using a centrifuge, and the thus obtained HPA crystals were washed with 100 parts by mass of water. As a result, 857.5 parts by mass of a filtrate was collected, and 91.9 parts by mass of a wet cake was obtained. The cake was dried at 30° C. in a nitrogen stream to obtain 71.3 parts by mass of the HPA crystal. A recovery of the HPA crystals based on the crude HPA was 44.1%. The crystals were analyzed by the gas chromatography (manufactured by Agilent Technologies Japan, Ltd.). As a result, the HPA crystals were found to contain 99.3% by mass of HPA, 0.00% by mass (below the detection limit) of neopentyl glycol, 0.00% by mass (below the detection limit) of isobutyric acid neopentyl glycol monoester, 0.50% by mass of neopentyl glycol hydroxypivalic acid monoester, 0.05% by mass of isobutyraldehyde, 0.00% by mass (below the detection limit) of formaldehyde, and 0.15% by mass of other components. The thus purified HPA crystals were mixed with water to prepare an HPA aqueous solution A containing 60% by mass of the purified HPA crystal.

<Production Example 3> (Preparation of Isobutyric Acid Neopentyl Glycol Monoester)

A mixture obtained by mixing 280.8 parts by mass of neopentyl glycol (a product of Mitsubishi Gas Chemical Company, Inc.), 79.0 parts by mass of pyridine (a product of Wako Pure Chemical Industries Ltd.), 12.2 parts by mass of N,N-dimethyl-4-aminopyridine (a product of Wako Pure Chemical Industries Ltd.) and 2500 parts by mass of methylene chloride (a product of Wako Pure Chemical Industries Ltd.) was set to 25° C. To this mixture, a methylene chloride solution containing 95.4 parts by mass of isobutyric acid chloride (a product of Wako Pure Chemical Industries Ltd.) was added dropwise over 4 hours. The resultant was stirred at 25° C. for 16 hours, and an unreacted portion of neopentyl glycol and impurities were removed by extraction using water. By analyzing a purity of a bottom product obtained by removing the solvent from the thus obtained oil layer by simple distillation, 96.4% by mass of isobutyric acid neopentyl glycol monoester and 3.60% by mass of other components were found to be contained.

<Reference Example 4> (First Cycle of Spiroglycol Synthesis)

116 parts by mass of pentaerythritol was dissolved in 1800 parts by mass of water, and methanesulfonic acid (a product of Wako Pure Chemical Industries Ltd.) was added thereto to make the resultant solution at pH 1.6. To the solution, 290 parts by mass of the HPA aqueous solution A prepared in Production Example 2 was added dropwise over 3 hours. A reaction temperature was set to 90° C. After completing the dropwise addition, the resultant solution was aged at 90° C. for 12 hours. After completing the aging, the resultant reaction solution was divided into 765 parts by mass and 1441 parts by mass, and the 1441 parts by mass of the reaction solution was solid-liquid separated to obtain 183 parts by mass of wet spiroglycol and 1130 parts by mass of a filtrate. Thereafter, the thus obtained wet spiroglycol was neutralized and washed with 500 parts by mass of a 500 ppm sodium hydroxide aqueous solution, and subsequently the resultant was washed with 500 parts by mass of water. Thereafter, the spiroglycol was dried. Incidentally, the 765 parts by mass of the reaction solution also contains spiroglycol crystals, and the spiroglycol crystals work as a seed crystal in the reaction of the subsequent second and later cycles.

<Reference Example 5> (Second to Fifteenth Cycles of Spiroglycol Synthesis)

765 parts by mass of the reaction solution obtained in the reaction of the first cycle, 1000 parts by mass of the filtrate obtained in the reaction of the first cycle, 25 parts by mass of water, 116 parts by mass of pentaerythritol and 0.7 parts by mass of methanesulfonic acid were mixed. Here, the resultant solution had pH 1.6. To this solution, 290 parts by mass of the HPA aqueous solution A was added dropwise over 3 hours. A reaction temperature was set to 90° C. After completing the dropwise addition, the resultant was aged at 90° C. for 3 hours. After completing the aging, the resultant reaction solution was divided into 765 parts by mass and remaining 1431.7 parts by mass, and the 1431.7 parts by mass of the reaction solution was solid-liquid separated to obtain 244 parts by mass of wet spiroglycol and 1083 parts by mass of a filtrate.

Then, also in the reaction of the third and later cycles, the reaction was repeatedly performed by mixing 765 parts by mass of the reaction solution obtained in the previous cycle, 1000 parts by mass of the filtrate, 25 parts by mass of water, 116 parts by mass of pentaerythritol and 0.7 parts by mass of methanesulfonic acid, and adding 290 parts by mass of the HPA aqueous solution A dropwise thereto over 3 hours. In the reaction of each cycle, about 80 to 90% by mass of the mother liquor of the whole reaction solution obtained in the previous cycle was used in the reaction of the next cycle. This synthesis reaction was repeatedly performed, and a stable mother liquor composition was obtained. In the reaction of the fifteenth cycle, the dried spiroglycol was obtained in an amount of 236 parts by mass in total. The yield of the spiroglycol based on the charged pentaerythritol (excluding the pentaerythritol contained in the filtrate) was 91.7% by mol.

The purity of the obtained spiroglycol was analyzed by the gas chromatography. As a result, the spiroglycol was found to contain 99.60 area % of spiroglycol, 0.01 area % of dioxane triol monoformal, 0.10 area % of hydroxypivalaldehyde neopentyl glycol acetal and 0.13 area % of spiro monoalcohol.

<Example 1> (Repeated Synthesis of Spiroglycol Using Purified HPA)

Figure 1:
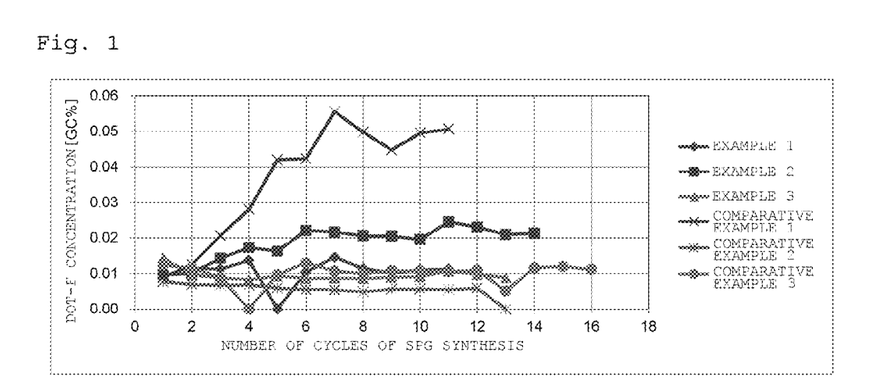
FIG. 1 shows a graph illustrating the number of cycles of SPG synthesis and change in DOT-F concentration obtained in examples and comparative examples.
Figure 2:
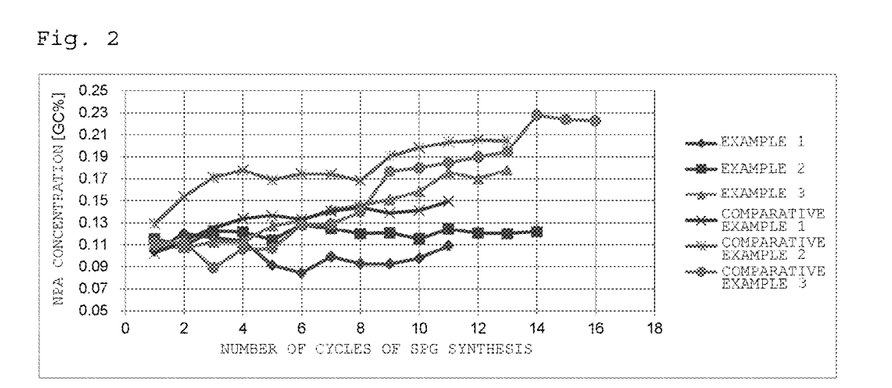
FIG. 2 shows a graph illustrating the number of cycles of SPG synthesis and change in NPA concentration obtained in the examples and the comparative examples.

The same synthesis as that of Reference Example 5 was performed by mixing 765 parts by mass of the reaction solution obtained in the reaction of the fifteenth cycle of Reference Example 5, 1000 parts by mass of the filtrate, 25 parts by mass of water, 116 parts by mass of pentaerythritol and 0.7 parts by mass of methanesulfonic acid, and adding 290 parts by mass of the HPA aqueous solution A dropwise thereto over 3 hours (corresponding to the first cycle of SPG synthesis illustrated in FIGS. 1 and 2). Then, 765 parts by mass of the reaction solution obtained by the reaction of this first cycle was used and mixed with 1000 parts by mass of the filtrate, 25 parts by mass of water, 116 parts by mass of pentaerythritol and 0.7 parts by mass of methanesulfonic acid, and 290 parts by mass of the HPA aqueous solution A was added dropwise over 3 hours to repeatedly perform the synthesis reaction of spiroglycol. This spiroglycol synthesis reaction was further repeated until an impurity concentration in the resultant spiroglycol was stabilized.

The gas chromatographic purity of the spiroglycol obtained in the eleventh cycle of the SPG synthesis was found to be 99.58 area % of spiroglycol, with 0.01 area % of dioxane triol monoformal, 0.11 area % of hydroxypivalaldehyde neopentyl glycol acetal and 0.14 area % of spiro monoalcohol. The results are shown in Table 1. Besides, the transition of the impurity concentration in the spiroglycol is illustrated in FIGS. 1 and 2.

<Example 2> (Repeated Synthesis of Spiroglycol with Addition of Formaldehyde to Purified HPA)

The purified HPA prepared in Production Example 2, water and formaldehyde were mixed to prepare an HPA aqueous solution B containing 60% by mass of the purified HPA and 0.33% by mass of formaldehyde per 100% by mass of the purified HPA. The synthesis reaction was repeated in the same manner as described in Example 1 except that the HPA aqueous solution B was used instead of the HPA aqueous solution A.

The gas chromatographic purity of the spiroglycol obtained in the fourteenth cycle was found to be 99.60 area % of spiroglycol, with 0.02 area % of dioxane triol monoformal, 0.12 area % of hydroxypivalaldehyde neopentyl glycol acetal and 0.14 area % of spiro monoalcohol. The results are shown in Table 1. Besides, the transition of the impurity concentration in the spiroglycol is illustrated in FIGS. 1 and 2.

<Example 3> (Repeated Synthesis of Spiroglycol with Addition of Isobutyric Acid Neopentyl Glycol Monoester to Purified HPA)

The purified HPA prepared in Production Example 2, water and isobutyric acid neopentyl glycol monoester were mixed to prepare an HPA aqueous solution C containing 60% by mass of the purified HPA and 0.58% by mass of isobutyric acid neopentyl glycol monoester per 100% by mass of the purified HPA. The synthesis reaction was repeated in the same manner as described in Example 1 except that the HPA aqueous solution C was used instead of the HPA aqueous solution A.

The gas chromatographic purity of the spiroglycol obtained in the thirteenth cycle was found to be 99.58 area % of spiroglycol, with 0.01 area % of dioxane triol monoformal, 0.18 area % of hydroxypivalaldehyde neopentyl glycol acetal and 0.15 area % of spiro monoalcohol. The results are shown in Table 1. Besides, the transition of the impurity concentration in the spiroglycol is illustrated in FIGS. 1 and 2.

<Comparative Example 1> (Repeated Synthesis of Spiroglycol with Addition of Formaldehyde to Purified HPA)

The purified HPA prepared in Production Example 2, water and formaldehyde were mixed to prepare an HPA aqueous solution D containing 60% by mass of the purified HPA and 0.83% by mass of formaldehyde per 100% by mass of the purified HPA. The synthesis reaction was repeated in the same manner as described in Example 1 except that the HPA aqueous solution D was used instead of the HPA aqueous solution A.

The gas chromatographic purity of the spiroglycol obtained in the eleventh cycle was found to be 99.41 area % of spiroglycol, with 0.05 area % of dioxane triol monoformal, 0.15 area % of hydroxypivalaldehyde neopentyl glycol acetal and 0.13 area % of spiro monoalcohol. The results are shown in Table 1. Besides, the transition of the impurity concentration in the spiroglycol is illustrated in FIGS. 1 and 2.

<Comparative Example 2> (Repeated Synthesis of Spiroglycol with Addition of Neopentyl Glycol to Purified HPA)

The purified HPA prepared in Production Example 2, water and neopentyl glycol were mixed to prepare an HPA aqueous solution E containing 60% by mass of the purified HPA and 2.50% by mass of neopentyl glycol per 100% by mass of the purified HPA. The synthesis reaction was repeated in the same manner as described in Example 1 except that the HPA aqueous solution E was used instead of the HPA aqueous solution A.

The gas chromatographic purity of the spiroglycol obtained in the thirteenth cycle was found to be 99.56 area % of spiroglycol, with 0.01 area % of dioxane triol monoformal, 0.20 area % of hydroxypivalaldehyde neopentyl glycol acetal and 0.13 area % of spiro monoalcohol. The results are shown in Table 1. Besides, the transition of the impurity concentration in the spiroglycol is illustrated in FIGS. 1 and 2.

<Comparative Example 3> (Repeated Synthesis of Spiroglycol with Addition of Hydroxypivalic Acid Neopentyl Glycol Monoester to Purified HPA)

The purified HPA prepared in Production Example 2, water and hydroxypivalic acid neopentyl glycol monoester were mixed to prepare an HPA aqueous solution F containing 60% by mass of the purified HPA and 2.50% by mass of hydroxypivalic acid neopentyl glycol monoester per 100% by mass of the purified HPA. The synthesis reaction was repeated in the same manner as described in Example 1 except that the HPA aqueous solution F was used instead of the HPA aqueous solution A.

The gas chromatographic purity of the spiroglycol obtained in the sixteenth cycle was found to be 99.54 area % of spiroglycol, with 0.01 area % of dioxane triol monoformal, 0.22 area % of hydroxypivalaldehyde neopentyl glycol acetal and 0.15 area % of spiro monoalcohol. The results are shown in Table 1. Besides, the transition of the impurity concentration in the spiroglycol is illustrated in FIGS. 1 and 2.

<Comparative Example 4> (Synthesis of Spiroglycol with Isobutyraldehyde Added to Purified HPA)

The purified HPA prepared in Production Example 2, water and isobutyraldehyde were mixed to prepare an HPA aqueous solution G containing 60% by mass of the purified HPA and 3.33% by mass of isobutyraldehyde per 100% by mass of the purified HPA. The synthesis reaction was performed in the same manner as described in Example 1 except that the HPA aqueous solution G was used instead of the HPA aqueous solution A.

The gas chromatographic purity of the spiroglycol obtained in the first cycle was found to be 96.20 area % of spiroglycol, with 0.01 area % of dioxane triol monoformal, 0.10 area % of hydroxypivalaldehyde neopentyl glycol acetal and 3.53 area % of spiro monoalcohol. The results are shown in Table 1.

TABLE 1

| | | Raw Material HPA | | | | | | Impurities in Spiroglycol | | |
| --- | --- | --- | --- | --- | --- | --- | --- | --- | --- | --- |
| | | HCHO [mass %] | IBD [mass %] | BNE [mass %] | NPG [mass %] | ESG [mass %] | BNE + NPG + ESG [mol/kg] | DOT-F [GC area %] | NPA [GC area %] | SPM [GC area %] |
| Example 1 | HPA Aqueous Solution A | — | 0.05 | — | — | 0.50 | 0.025 | 0.00-0.01 | 0.08-0.12 | 0.12-0.14 |
| Example 2 | HPA Aqueous Solution B | 0.33 | 0.05 | — | — | 0.50 | 0.025 | 0.02-0.03 | 0.12 | 0.14 |
| Example 3 | HPA Aqueous Solution C | — | 0.05 | 0.58 | — | 0.50 | 0.058 | 0.01 | 0.17-0.18 | 0.14-0.15 |
| Comparative Example 1 | HPA Aqueous Solution D | 0.83 | 0.05 | — | — | 0.50 | 0.025 | 0.05-0.06 | 0.14-0.15 | 0.12-0.14 |

TABLE 1-continued

| | | Raw Material HPA | | | | | Impurities in Spiroglycol | | |
| | | HCHO [mass %] | IBD [mass %] | BNE [mass %] | NPG [mass %] | ESG [mass %] | BNE + NPG + ESG [mol/kg] | DOT-F [GC area %] | NPA [GC area %] | SPM [GC area %] |
|---|---|---|---|---|---|---|---|---|---|---|
| Comparative Example 2 | HPA Aqueous Solution E | — | 0.05 | — | 2.50 | 0.50 | 0.265 | 0.00-0.01 | 0.20 | 0.12-0.13 |
| Comparative Example 3 | HPA Aqueous Solution F | — | 0.05 | — | — | 2.50 | 0.123 | 0.01 | 0.22-0.23 | 0.15 |
| Comparative Example 4 | HPA Aqueous Solution G | — | 3.33 | — | — | 0.50 | 0.025 | 0.01 | 0.10 | 3.53 |

Abbreviations used in Table 1 and FIGS. 1 and 2 are as follows. Incidentally, each amount in % by mass or the like of HCHO, IBD, BNE, NPG and ESG in the raw material HPA shown in Table 1 is shown not as a proportion to the whole 60% HPA aqueous solution including water but as a value based on the total amount of the raw material hydroxypivalaldehyde.

DOT-F: dioxane triol monoformal
NPA: hydroxypivalaldehyde neopentyl glycol acetal
SPM: spiro monoalcohol
HCHO: formaldehyde
IBD: isobutyraldehyde
BNE: isobutyric acid neopentyl glycol monoester
NPG: neopentyl glycol
ESG: hydroxypivalic acid neopentyl glycol monoester As described above, it was found that in the synthesis of spiroglycol, when the contents of impurities, that is, formaldehyde, neopentyl glycol, an ester compound having a neopentyl glycol skeleton and isobutyraldehyde, contained in raw material HPA are controlled, generation of various acetal compounds, that is, by-products, generated in synthesis of the diol having the cyclic acetal skeleton is inhibited, and thus a high purity spiroglycol can be obtained. Incidentally, also in Comparative Example 4, there was a tendency similar to the other comparative examples.

Besides, when an experiment similar to that of the spiroglycol was performed particularly on dioxane glycol, it was confirmed that a compound resulting from an acetalization reaction of isobutyraldehyde and trimethylolpropane, neopentyl glycol and a compound derived from an ester compound having a neopentyl glycol skeleton were produced as by-products. Also the synthesis of the diol having the cyclic acetal skeleton such as dioxane glycol proceeds through substantially a similar reaction path, and therefore, it is thus analogized that the generation of various acetal compounds, that is, by-products, in the synthesis of the diol having the cyclic acetal skeleton can be inhibited by controlling neopentyl glycol, an ester compound having a neopentyl glycol skeleton, isobutyraldehyde and the like.

The present application is based upon the Japanese patent application (Japanese Patent Application No. 2016-050882) filed with Japan patent office on Mar. 15, 2016, the entire contents of which are incorporated herein by reference.

INDUSTRIAL APPLICABILITY

A spiroglycol is a polyhydric alcohol having a cyclic acetal in a molecule, and is a compound useful as an intermediate of a polymer material such as polycarbonate, polyester, polyacrylate, polyurethane, polyether polyol, an epoxy resin or the like, or as a monomer, or further as a raw material of an adhesive, a plasticizer, a resin stabilizer, a lubricant or the like. Accordingly, the present invention has industrial applicability in at least these uses.

The invention claimed is:

1. A method for producing a diol having a cyclic acetal skeleton, the method comprising:
   conducting a first acetalization reaction of a raw material hydroxypivalaldehyde and at least pentaerythritol and/or trimethylolpropane under an acid catalyst, to obtain a reaction solution comprising the diol having the cyclic acetal skeleton;
   separating the diol having the cyclic acetal skeleton, which is precipitated in the reaction solution, to obtain a reaction mother liquor; and
   conducting a second acetalization reaction of a rain material hydroxypivalaldehyde and at least pentaerythritol and/or trimethylolpropane under the reaction mother liquor and an acid catalyst, to obtain the diol having the cyclic acetal skeleton,
   wherein the separating and the second acetalization reaction are conducted more than once,
   wherein the raw material hydroxypivalaldehyde comprises an impurity selected from the group consisting of formaldehyde, neopentyl glycol, isobutyraldehyde and an ester compound having a neopentyl glycol skeleton of formula (III):

(III)

wherein R represents a hydrocarbon group having 1 to 4 carbon atoms, a hydrocarbon group having a hydroxy group and having 1 to 4 carbon atoms, or a hydrogen atom, and
   wherein when the impurity comprises the formaldehyde, a content of the formaldehyde is 0.80% by mass or less;
   when the impurity comprises the neopentyl glycol and/or the ester compound, a total molar concentration of the neopentyl glycol and/or the ester compound is 0.100 mol/kg or less; and
   when the impurity comprises the isobutyraldehyde, a content of the isobutyraldehyde is 0.05% by mass or less,
   all based on 100% by mass of the raw material hydroxypivalaldehyde.

2. The method according to claim 1, wherein the diol obtained by the second acetalization reaction comprises, as an impurity, a dioxane triol monoformal of formula (I) in an amount of 004 area % or less, expressed as an area fractional concentration based on a sum of components having a relative retention time of 1.45 or less in a gas chromatography analysis performed under prescribed conditions in which the relative retention time of the diol is 1.00:

(I)

3. The method according to claim 1, wherein the diol obtained by the second acetalization reaction comprises, as an impurity, a hydroxypivalaldehyde neopentyl glycol acetal of formula (II) in an amount of 0.19 area % or less, expressed as an area fractional concentration based on a sum of components having a relative retention time of 1.45 or less in a gas chromatography analysis performed under prescribed conditions in which the relative retention time of the diol is 1.00:

(II)

4. The method according to claim 1, wherein the diol obtained by the second acetalization reaction comprises, as an impurity, a spiro monoalcohol of formula (IV) in an amount of 0.15 area % or less, expressed as an area fractional concentration based on a sum of components having a relative retention time of 1.45 or less in a gas chromatography analysis performed under prescribed conditions in which the relative retention time of the diol is 1.00:

(IV)

5. The method according to claim 1, wherein the ester compound comprises
an isobutyric acid neopentyl glycol monoester of formula (V):

(V)

and/or
a hydroxypivalic acid neopentyl glycol monoester of formula (VI):

(VI)

6. The method according to claim 1, wherein the diol is spiroglycol and/or dioxane glycol.

7. The method according to claim 1, the method further comprising:
conducting an aldol condensation reaction for forming crude hydroxypivalaldehyde by an aldol condensation reaction of formaldehyde and isobutyraldehyde.

8. The method according to claim 7, the method further comprising, at least any one of:
extracting the raw material hydroxypivalaldehyde by adding water and/or an organic solvent to the crude hydroxypivalaldehyde;
distilling the crude hydroxypivalaldehyde to collect the raw material hydroxypivalaldehyde as a distillate; and
crystallizing the raw material hydroxypivalaldehyde by adding water and/or an organic solvent to the crude hydroxypivalaldehyde and collecting the raw material hydroxypivalaldehyde by solid-liquid separation.

9. The method according to claim 1, wherein a reaction temperature employed during the acetalization reaction is from 40° C. to 105° C.,
wherein a pH value of a reaction solution during the acetalization reaction is from 0.1 to 4.0, and
wherein after the first acetalization reaction, 30 to 98% by mass of the reaction mother liquor is reused to perform the second acetalization reaction.

* * * * *